(12) United States Patent
Osaka et al.

(10) Patent No.: US 8,148,160 B2
(45) Date of Patent: Apr. 3, 2012

(54) ELECTRODE FOR MOLECULAR SENSING AND METHOD FOR MOLECULAR SENSING

(75) Inventors: Tetsuya Osaka, Tokyo (JP); Mariko Matsunaga, Tokyo (JP); Tsubasa Ueno, Tokyo (JP)

(73) Assignee: Waseda University, Tokyo (JP)

( * ) Notice: Subject to any disclaimer, the term of this patent is extended or adjusted under 35 U.S.C. 154(b) by 0 days.

(21) Appl. No.: 12/328,583

(22) Filed: Dec. 4, 2008

(65) Prior Publication Data
US 2010/0144047 A1    Jun. 10, 2010

(51) Int. Cl.
*G01N 27/26* (2006.01)
(52) U.S. Cl. ............ 436/96; 436/91; 436/152; 436/151; 436/150; 436/149
(58) Field of Classification Search .............. 436/152, 436/151, 150, 149, 96, 91; 422/82.03, 82.01; 73/53.01; 204/403.1, 403.14
See application file for complete search history.

(56) References Cited

U.S. PATENT DOCUMENTS
5,443,701 A * 8/1995 Willner et al. ............. 205/777.5
2007/0227907 A1 * 10/2007 Shah et al. ................. 205/777.5

OTHER PUBLICATIONS

Wang, Yunxia; et al. "Probing chiral amino acids at sub-picomolar level based on bovine serum albumin enantioselective films coupled with silver-enhanced gold nanoparticles." Talanta 69 (Apr. 2006) p. 1240-1245.*

Limanskii, A. P.; et al. "Functionalization of amino-modified probes for atomic force microscopy." Molecular Biophysics 51 (Apr. 2006) p. 186-195.*
Cox, James A.; et al. "Measurement platforms fabricated by layer-by-layer assembly of crown ether functionalized gold nanoclusters." Journal of Solid State Electrochemistry 8 (2004) p. 722-726.*
Corry, Bobby; et al. "Probing direct binding affinity in electrochemical antibody-based sensors." Analytica Chimica Acta 496 (2003) p. 103-116.*
Kumar, Arun; et al. "Tetraethylorthosilicate film modified with protein to fabricate cholesterol biosensor." Talanta 69 (Dec. 2005) p. 700-705.*
Mena, M. L. et al. "Laccase biosensor based on N-succinimidyl-3-thiopropionate-functionalized gold electrodes." Electroanalysis (2005) 17 2147-2155.*
Mariko Matsunaga et al., "Enantioselective potential response of a human serum albumin-modified ITO electrode for tryptophan", Electrochemistry Communications 10, 2008, pp. 1844-1846.
Sho Hideshima et al., "Enantioselective potential response of a human serum albumin-modified oxide electrode", The Seventh International Symposium on Electrochemical Micro & Nano-system Technologies. (2008).

(Continued)

*Primary Examiner* — Yelena G Gakh
*Assistant Examiner* — Christopher A Hixson
(74) *Attorney, Agent, or Firm* — Birch, Stewart, Kolasch & Birch, LLP

(57) ABSTRACT

Molecular sensing of target molecules is performed by using an electrode for molecular sensing in which detecting molecules which can shift a surface potential of the electrode by an interaction with the target molecules are bound directly or via coupling molecules to surface hydroxyl groups on a conductive metal oxide. By this molecular sensing, specific target molecules can be detected selectively and stably with high accuracy. It is also possible to detect an enantiomer selectively and stably with high accuracy. The present invention can provide a chemical sensing system which is useful in fields such as medicines, environments and foods.

10 Claims, 4 Drawing Sheets

OTHER PUBLICATIONS

Tsubasa Ueno et al., "Enantioselective potential response of albumin modified ITO electrode with addition of Trp", The 75$^{th}$ Annual Meeting of the Electrochemical Society of Japan, pp. 179. (2008).

"Chiral recognition with albumin-modified ITO electrode", The 2$^{nd}$ Kanto Branch Meeting of the Chemical Society of Japan. (2008).

"Molecular Modification of ITO electrode for Chiral Discrimination", The 28$^{th}$ Annual Meeting of the Surface Science Society of Japan. (2008).

* cited by examiner

ELECTRODE FOR MOLECULAR SENSING AND METHOD FOR MOLECULAR SENSING

BACKGROUND OF THE INVENTION

1. Field of the Invention

This invention relates to an electrode for molecular sensing, which can selectively detect molecules with high sensitivity, especially to an electrode for molecular sensing, which can selectively detect an enantiomer with high sensitivity, and also to a method for molecular sensing by using the electrode.

2. Prior Art

In fields such as medicines, environments and foods, there has been a strong demand for the development of a chemical sensing system that can selectively detect a specific chemical substance, and in recent years, research is under way toward its realization with objectives placed on improvements in detection sensitivity and accuracy. Among such research, electrochemical sensors using metal electrodes such as Au, carbon electrodes, semiconductor electrodes and the like are expected to find wide applications, because they can detect the signal quickly. Further, there is also an outstanding desire for the development of an electrode for molecular sensing and a method for molecular sensing, which make it possible to selectively and stably detect target molecules, and moreover, which can perform chiral recognitions.

SUMMARY OF THE INVENTION

In case of using an electrode of an electrochemical sensor for molecular sensing, it is necessary to modify the surface of the electrode with a molecular recognition substance. The modification of solid surfaces with various molecules is an effective method from the viewpoint of providing electrodes with a molecular recognition function. As these molecular recognition substances, biomolecules, biologically-relevant substances, supermolecules, highly functional molecules, organic monolayers and the like are used. When target molecules include enantiomers, enantioselectivity is required for the molecular recognition substance.

An object of the present invention is to provide an electrode for molecular sensing, which makes it possible to selectively and stably detects specific target molecules with high sensitivity, especially an electrode for molecular sensing, which can selectively detect enantiomers with high sensitivity, and also a method for molecular sensing by using the electrode.

In a first aspect of the present invention, there is provided an electrode for molecular sensing, wherein detecting molecules capable of shifting a surface potential of the electrode by an interaction with target molecules are bound directly or via coupling molecules to surface hydroxyl groups on a conductive metal oxide.

In a second aspect of the present invention, there is also provided a method for molecular sensing, which includes using the electrode for molecular sensing according to the first aspect, and based on a shift in the surface potential of the electrode, detecting target molecules.

In molecular sensing by using the electrode, the surface potential of the electrode shifts through an interaction between the detecting molecules and target molecules at a molecule detection site when the target molecules come close to the detecting molecules bound on the surface of the electrode. Detection of this potential shift enables molecular sensing.

The detecting molecules may be bound directly to the surface hydroxyl groups on the conductive metal oxide. It is, however, particularly preferred that the detecting molecules are bound to the surface hydroxyl groups via an aminoalkylalkoxysilane as coupling molecules.

As the detecting molecules, a succinimidyl-group-containing compound can be used. In this case, it is possible to perform effective molecular sensing of an indole-ring-containing compound such as tryptophan, tryptamine or indolepropionic acid. Further, it is more preferred to perform the molecular sensing of the target molecules in an aqueous solution of pH 7 to 10.

A third aspect of the present invention is to provide an electrode for molecular sensing, wherein detecting molecules capable of shifting a surface potential of the electrode by an interaction with target molecules are bound directly or via coupling molecules to surface hydroxyl groups on a conductive metal oxide, and a part of the detecting molecules are modified with modifying molecules that make the shift in the surface potential different depending upon whether the target molecules are a D-enantiomer or L-enantiomer.

A fourth aspect of the present invention is to provide a method for molecular sensing, which includes using an electrode for molecular sensing according to the third aspect of the present invention, and based on a shift in the surface potential of the electrode, selectively detecting a D-enantiomer or L-enantiomer as the target molecules.

By modifying a part of the detecting molecules with modifying molecules that make the shift in the surface potential different depending upon whether the target molecules are a D-enantiomer or L-enantiomer, the molecular sensing of the enantiomer can be performed chiral-selectively.

The detecting molecules may be bound directly to the surface hydroxyl groups on the conductive metal oxide. It is, however, particularly preferred that the detecting molecules are bound to the surface hydroxyl groups via an aminoalkylalkoxysilane as coupling molecules.

As the detecting molecules, a succinimidyl-group-containing compound can be used. In this case, the use of human serum albumin, a modifying molecule, makes it possible to perform chiral-selective molecular sensing of an enantiomeric indole-ring-containing compound as target molecules, such as D-tryptophan or L-tryptophan. Further, it is more preferred to perform the molecular sensing of the target molecules in an aqueous solution of pH 7 to 10.

According to the present invention, specific target molecules can be selectively and stably detected with high accuracy, and further, an enantiomer can be selectively and stably detected with high accuracy. According to the present invention, it is thus possible to provide a chemical sensing system which is useful in fields such as medicines, environments and foods.

DESCRIPTION OF PREFERRED EMBODIMENTS

Figure 1:
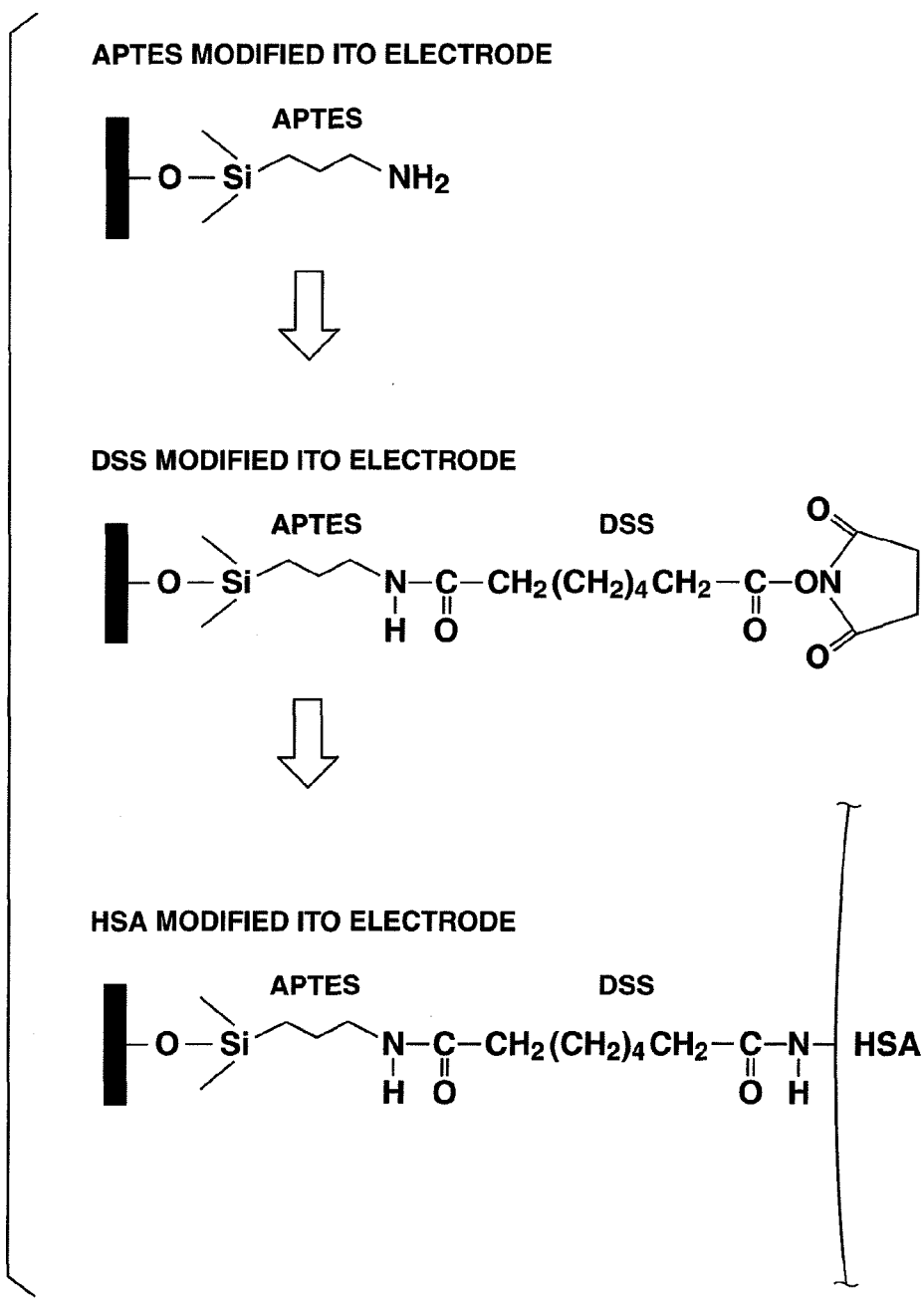
FIG. 1 is a schematic illustrating a state that APTES is bound to a surface hydroxyl group of an ITO electrode, a state that DSS is bound to the APTES, and a state that the DSS has been modified with HSA.

In the electrode according to the present invention for molecular sensing, the detecting molecules which substantially make up a detecting portion of the electrode for molecular sensing are fixed on a surface of the conductive metal oxide. This conductive metal oxide is also a conductive portion for detecting the surface potential shift of the electrode. The conductive metal oxide may form an electrode substrate by itself, or may be formed on a surface of a material other than conductive metal oxides to provide an electrode substrate.

Examples of the conductive metal oxide include ITO (indium tin oxide), tin oxides (for example, $SnO_2$), and indium oxides (for example, $In_2O_3$). In addition, zinc oxide (ZnO)-based metal oxides are also usable. Of these, ITO is particularly preferred.

In the electrode according to the present invention for molecular sensing, the detecting molecules are bound directly or via the coupling molecules to the surface hydroxyl groups on the conductive metal oxide. The detecting molecules act to shift the surface potential of the electrode through an interaction with the target molecules (for example, an electrical interaction or binding resulting in a change in intramolecular polarization).

The conductive metal oxide has hydroxyl groups on its surface, and the surface hydroxyl groups can bind to detecting molecules directly or via the coupling molecules. To make more effective use of the surface of the conductive metal oxide so that the sensitivity of sensing can be improved, cleaning treatment is generally applied to the surface of the conductive metal oxide.

As this cleaning treatment, it is possible to make combined use of, for example, treatment that cleans the surface of the conductive metal oxide with an organic solvent optionally by using ultrasonic waves as needed, and/or $O_2$ plasma ashing processing of the surface of the conductive metal oxide, and/or the like as desired.

When binding the detecting molecules directly to the surface hydroxyl groups on the conductive metal oxide, the detecting molecules are required to have functional groups that react to the surface hydroxyl groups. The reaction between the detecting molecules and the surface hydroxyl groups is feasible, for example, by bringing the surface of the conductive metal oxide, which carries the hydroxyl groups thereon, into contact with a solution (organic solvent solution) containing the detecting molecules.

On the other hand, when the detecting molecules do not have functional groups that react to hydroxyl groups, the detecting molecules can be bound to the surface hydroxyl groups using the coupling molecules that crosslink the detecting molecules. The coupling molecules can be used either alone or in connected forms of two or more kinds.

It is necessary for at least one kind of coupling molecules to include a functional group reactive to the surface hydroxyl group at an end thereof and a functional group reactive to the detecting molecule at an opposite end thereof. As the functional group reactive to the surface hydroxyl group, an alkoxy group is preferable. As the functional group which is contained at the opposite end of the coupling molecule and is reactive to the detecting molecule, an amino group, carboxyl group or the like is particularly preferred. Amino groups or carboxyl groups are preferred in that they can be bound to carboxyl groups or amino groups, respectively, and especially in that they are functional groups contained in biologically-relevant molecules and biomolecules such as amino acids and proteins.

The coupling molecules may preferably be an aminoalkylalkoxysilane that one to three aminoalkyl groups preferably having from one to five carbon atoms and one to three alkoxy groups preferably having from one to three carbon atoms are bonded to silicon atoms. This aminoalkylalkoxysilane may have one or two alkyl groups (methyl group(s), ethyl group(s) or the like) bonded to a silicon atom, and an aminoalkyltrialkoxysilane is particularly preferred. More specifically, aminopropyltrimethoxysilane (APTMS) and aminopropyltriethoxysilane (APTES) can be mentioned. When an aminoalkylalkoxysilane is used as coupling molecules, the aminoalkylalkoxysilane can be formed as a monolayer on the surface of the conductive metal oxide.

The reaction between the coupling molecules and the surface hydroxyl groups can be conducted, for example, by bringing the surface of the conductive metal oxide, which carries the hydroxyl groups, into contact with a solution (for example, an organic solvent solution) containing the coupling molecules. For example, when aminopropyltrimethoxysilane or aminopropyltriethoxysilane is used, the contact can be effected, for example, at a temperature of from room temperature (e.g., 20° C.) to a temperature lower than the boiling point of the solution (e.g., 60° C. or so in the case of an ethanol solution) in a 0.01 to 5 wt %, especially 0.1 to 3 wt % solution in an alcohol (for example, methanol, ethanol or the like).

When the coupling molecules are used, the coupling molecules and the detecting molecules are bound with each other. It is necessary for the detecting molecules to have functional groups that react to the functional groups at the opposite ends of the coupling molecules. As mentioned above, when the functional groups at the opposite ends of the coupling molecules are amino groups or carboxyl groups, the detecting molecules can be bound to the respective functional groups at the opposite ends provided that the detecting molecules have carboxyl groups or amino groups.

Various detecting molecules can be selected depending on the target molecules. For example, when the target molecules are an indole-ring-containing compound, a succinimidyl-group-containing compound is suited as detecting molecules. Preferred as the succinimidyl-group-containing compound is a disuccinimidyl alkylenedicarboxylate that the hydrogen atoms of the carboxyl groups of an alkylenedicarboxylic acid—which has the carboxyl groups at the opposite ends of a linear alkylene group of from two to ten carbon atoms, especially form four to eight carbon atoms—have been substituted by succinimidyl groups, respectively. As this disuccinimidyl alkylenedicarboxylate, disuccinimidyl suberate (DSS) can be mentioned, for example.

On the other hand, the indole-ring-containing compound as target molecules is not limited insofar as it contains an indole ring therein. However, indole rings each of which contains a substituent group, especially indole rings each of which contains a substituent group at the 3-position thereof, such as tryptophan, tryptamine and indolepropionic acid can be mentioned. In particular, this substituent group may preferably be an amino group, a carboxyl group, or a hydrocarbon group having an amino group, a carboxyl group or both of an amino group and a carboxyl group. Exemplary hydrocarbon group contains one to six carbon atoms, especially one to three carbon atoms, and a linear alkyl group is preferred. Specifically, 2-aminoethyl, 2-hydroxycarbonylethyl and 2-amino-(2-hydroxycarbonyl)ethyl can be mentioned. In addition, as the indole-ring-containing compound, biologically-relevant substances such as serotonin, alkaloid, auxin and indomethacin can be mentioned.

When a disuccinimidyl alkylenedicarboxylate is used as detecting molecules, use of one having an amino group at a coupling molecule at the above-mentioned opposite end results in a reaction between the amino group and the disuccinimidyl alkylenedicarboxylate, so that one of the succinimidyl group is eliminated and an amide bond is formed between the remaining carboxyl group and the amino group to couple the coupling molecule and the detecting molecule together.

The reaction between these coupling molecules and detecting molecules is feasible, for example, by bringing the coupling molecules, which are bound to the hydroxyl groups on the surface of the conductive metal oxide, into contact with a solution containing such detecting molecules (for example, an organic solvent solution). When aminopropyltrimethoxysilane or aminopropyltriethoxysilane is used as coupling molecules and disuccinimidyl suberate is used as detecting molecules, for example, it is only necessary to maintain the coupling molecules in contact with the detecting molecules in a 0.1 to 100 mmol/L, especially 1 to 50 mmol/L solution of disuccinimidyl suberate in DMF, under an inert gas atmosphere such as Ar, at a temperature, for example, of room temperature (e.g., 20° C.) or so, for, for example, one to 24 hours, especially two to 12 hours.

In the present invention, the detecting molecules can be either biomolecules or non-biomolecules. However, non-biomolecules are preferred, because in the case of biomolecules, electrochemical signals may be lost due to lo their size and complex structure so that a sufficient sensitivity may not be available.

In the electrode for molecular sensing according to the present invention, a portion of the detecting molecules may be modified with modifying molecules that make the shift in the surface potential of the electrode different depending upon whether the target molecules are a D-enantiomer or L-enantiomer. By modifying a portion of the detecting molecules with modifying molecules having chiral selectivity, that is, modifying molecules the coordination state of which differs depending upon whether the target molecules are a D-enantiomer or L-enantiomer (biomolecules can be mentioned as such modifying molecules), the interaction between the detecting molecules and target molecules differs by an interaction (the coordination state) between the target molecules and the adjacent modifying molecules depending upon whether the target molecules are a D-enantiomer or L-enantiomer. Based on this difference, the enantiomers can be detected chiral-selectively.

The modifying molecules can be selected from various modifying molecules depending upon the target molecules and detecting molecules. When the target molecules are an indole-ring-containing compound having enantiomers and the detecting molecules are a succinimidyl-group-containing compound, for example, human serum albumin (HSA) is preferred.

When human serum albumin is used as modifying molecules and a disuccinimidyl alkylenedicarboxylate is used as detecting molecules, the residual groups of the disuccinimidyl alkylenedicarboxylate coupled with the coupling molecules reacts to human serum albumin, so that the remaining succinimidyl groups (at the opposite ends) out of the residual groups are eliminated and amide bonds are formed between the remaining carboxyl groups and amino groups in the human serum albumin. Through the amide bonds, the detecting molecules and the modifying molecules can be coupled to modify the detecting molecules.

As the indole-ring-containing compound as target molecules in this case, the above-mentioned indole-ring-containing compound can be mentioned. In particular, D-enantiomers and L-enantiomers of indole-ring-containing compounds having enantiomers, for example, D-tryptophan and L-tryptophan can be mentioned as suitable indole-ring-containing compounds.

The reaction between the detecting molecules and the modifying molecules is feasible, for example, by bringing the detecting molecules (the detecting molecules bound to the hydroxyl groups on the surface of the conductive metal oxide either directly or via coupling molecules) into contact with a solution containing the modifying molecules (for example, an aqueous solution in a phosphate buffer or the like). When disuccinimidyl suberate is used as detecting molecules and human serum albumin is used as modifying molecules, for example, it is only necessary to maintain the disuccinimidyl suberate in contact with the human serum albumin in a 1 to 100 mg/mL, especially 5 to 50 mg/mL solution in a phosphate buffer (an aqueous solution), at a temperature, for example, of room temperature (e.g., 20° C.) or so, for, for example, from 0.5 to 12 hours, especially from one to six hours.

Biomolecules often show high substance selectivity. In the method that electrochemically detects a product formed by a reaction between target molecules and biomolecules as detecting molecules, the method that electrochemically detects target molecules held on biomolecules, and like methods, however, electrochemical signals may be lost due to the size and complex structure of the biomolecules so that sufficient sensitivity may not be obtained in some instances.

On the other hand, the use of non-biomolecules as detecting molecules and biomolecules (especially, biomolecules having chiral (stereo) selectivity or structure selectivity) as modifying molecules makes it possible to differentiate the coordination states of the D-enantiomer and L-enantiomer under the action of the biomolecules as the modifying molecules having the chiral (stereo) selectivity or structure selectivity so that a substantial potential shift can be detected based on an interaction (recognition reaction) with the non-biomolecules as the detecting molecules. This method is allowed to effectively function as a system for sensing macromolecules such as biomolecules as target molecules without using biomolecules as detecting molecules.

As a method for sensing target molecules by using the electrode for molecular sensing according to the present invention, the sensing of the target molecules can be performed by firstly measuring the potential ($E_0$) in a stable state before addition of target molecules with a three-electrode cell wherein there are immersed the above-mentioned electrode for molecular sensing according to the present invention as a working electrode (WE), an Ag/AgCl electrode as an illustrative reference electrode (RE) and a Pt wire as an illustrative counter electrode (CE) in an aqueous electrolyte solution, for example, an aqueous solution of a phosphate salt such as a phosphate buffered saline (PBS), then monitoring the potential (E) for a predetermined time after addition of the target molecules to the aqueous electrolyte solution (for example, dropwise addition of an aqueous solution containing the target molecules to the aqueous electrolyte solution), and determining the difference in potential ($\Delta E = E - E_0$) before and after the addition of these target molecules. Especially, when an electrode for molecular sensing with a portion of sensing molecules modified with modifying molecules is used, the above-described difference in potential differs depending on whether the target molecules are the D- or the L-enantiomer. Based on this difference in potential, chiral (stereo) selective sensing of the enantiomers can be performed.

The concentration of the target molecules in the detection atmosphere (the aqueous electrolyte solution) can range over a wide range of from 1 nmol/L to 10 mmol/L. At 100 μmol/L and higher, particularly good detection can be performed.

In molecular sensing, the pH of a detection atmosphere in which target molecules are to be detected (the pH of an aqueous electrolyte solution containing the target molecules) may range preferably from 7 to 10, notably from 7.4 to 9. As the aqueous electrolyte solution, a phosphate buffer, a borate buffer or the like can be used. Especially, when the sensing of an indole-ring-containing compound having enantiomers is performed by using a disuccinimidyl alkylenedicarboxylate as detecting molecules and human serum albumin as modifying molecules, the difference in potential ($\Delta E$) between the D-enantiomer and the L-enantiomer becomes clear when the pH is about 8, so that the enantiomers can be detected more selectively with high sensitivity. This pH level is, therefore, particularly preferred.

The electrode and method for molecular sensing according to the present invention are useful in a chemical sensing system for detecting specific chemical substances, for example, biomolecules and biologically-related substances, especially enantiomers in fields such as medicine, environments and foods.

EXAMPLES

The present invention will hereinafter be specifically described based on Examples, although the present invention shall not be limited to the following Examples.

Example 1

<Preparation of Electrode for Molecular Sensing>

An ITO substrate (size: 10 mm×10 mm×0.7 mm (thick)) was provided, and was ultrasonically washed with methanol and acetone, respectively, in this order for five minutes per solvent. Next, the washed ITO substrate was cleaned further at a surface thereof by $O_2$ plasma ashing (200 W, three minutes).

The cleaned ITO substrate was then immersed at 60° C. for 15 minutes in a 1 wt % solution of aminopropyltriethoxysilane (APTES) in ethanol to form a monolayer of aminopropyltriethoxysilane on the surface of the ITO substrate so that coupling molecules are bound.

After cleaning the surface of the ITO substrate with ethanol, the ITO substrate was immersed in a 10 mmol/L solution of disuccinimidyl suberate (DSS) in DMF at room temperature for eight hours under an Ar atmosphere so that disuccinimidyl suberate was bound as detecting molecules to aminopropyltriethoxysilane to prepare an electrode for molecular sensing. In FIG. 1, there is shown a schematic of a state that APTES is bound to a surface hydroxyl group of the ITO electrode and also of a state that DSS bound to the APTES.

<Molecular Sensing>

Immersed in a phosphate buffer (PBS) of pH 7.4 were the above-obtained electrode for molecular sensing as a working electrode (WE), an Ag/AgCl electrode as a reference electrode (RE), and a Pt wire as a counter electrode (CE). The potential ($E_0$) before addition of target molecules was then measured at room temperature in an Ar atmosphere.

Figure 2:
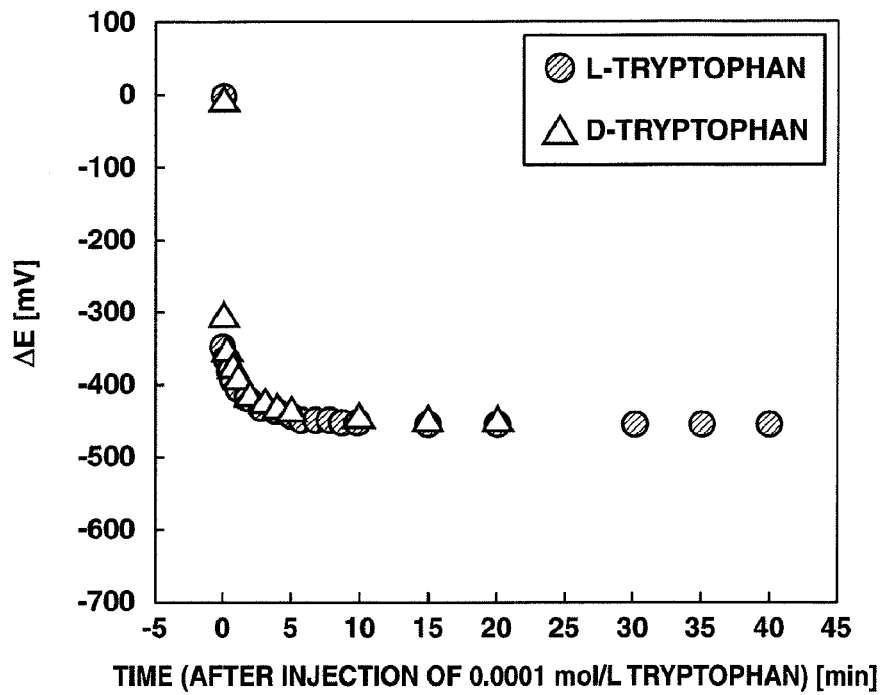
FIG. 2 is a graph showing changes with time in potential shift in Examples 1 and 2.

D-tryptophan was then added as target molecules such that its concentration in the phosphate buffer became 0.0001 mol/L, and the potential (E) was measured at time intervals. Potential shifts ($\Delta E = E - E_0$) are shown in FIG. 2.

Example 2

In a similar manner as in Example 1 except that the target molecules were changed to L-tryptophan, the potential ($E_0$) and potential (E) were measured. Potential shifts ($\Delta E$) are shown in FIG. 2.

Example 3

In a similar manner as in Example 1 except that the target molecules were changed to tryptamine, the potential ($E_0$) and potential (E) were measured. The potential shift ($\Delta E$) at the time point that the potential no longer changed by ±0.5 mV or more for 5 minutes (upon elapsed time of 15 minutes) subsequent to the addition of the tryptamine was −507 mV.

Example 4

In a similar manner as in Example 1 except that the target molecules were changed to indolepropionic acid, the potential ($E_0$) and potential (E) were measured. The potential shift ($\Delta E$) at the time point that the potential no longer changed by ±0.5 mV or more for 5 minutes (upon elapsed time of 40 minutes) subsequent to the addition of the indolepropionic acid was −396 mV.

From the results of Examples 1 to 4, it is appreciated that the electrode for molecular sensing according to the present invention is effective for the detection of indole-ring-containing compounds.

Examples 5 and 6

In a similar manner as in Example 1 except that the concentration of D-tryptophan in the phosphate buffer was changed to 0.001 mol/L (Example 5) and 0.01 mol/L (Example 6), respectively, the potential ($E_0$) and potential (E) were measured. The potential shifts ($\Delta E$) at the time points that the potentials no longer changed by ±0.5 mV or more for 5 minutes (upon elapsed time of 20 minutes) subsequent to the addition of the D-tryptophan are shown in FIG. 3 together with the results of Example 1.

Examples 7 and 8

In a similar manner as in Example 2 except that the concentration of L-tryptophan in the phosphate buffer was changed to 0.001 mol/L (Example 7) and 0.01 mol/L (Example 8), respectively, the potential ($E_0$) and potential (E) were measured. The potential shifts ($\Delta E$) at the time points that the potentials no longer changed by ±0.5 mV or more for 5 minutes subsequent to the addition of the L-tryptophan are shown in FIG. 3 together with the results of Example 2.

Figure 3:
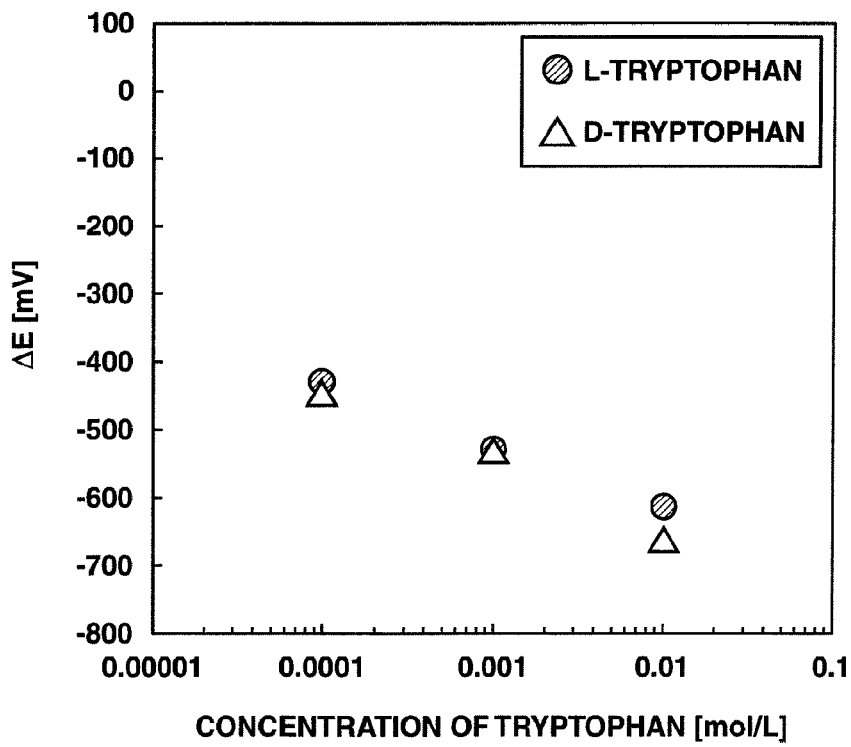
FIG. 3 is a graph illustrating potential shifts in Examples 1, 2 and 5 to 8 and showing the concentration dependency of the potential shift on the target molecules.

As the potential shift changes depending upon the concentration of target molecules as shown in FIG. 3, it is appreciated that the concentration of target molecules can be measured by the molecular sensing of the present invention.

Example 9

<Preparation of Electrode for Molecular Sensing>

An ITO substrate (size: 10 mm×10 mm×0.7 mm (thick)) was provided, and was ultrasonically washed with methanol and acetone, respectively, in this order for five minutes per solvent. Next, the washed ITO substrate was cleaned further at a surface thereof by $O_2$ plasma ashing (200 W, three minutes).

The cleaned ITO substrate was then immersed at 60° C. for 15 minutes in a 1 wt % solution of aminopropyltriethoxysilane (APTES) in ethanol to form a monolayer of aminopropyltriethoxysilane on the surface of the ITO substrate so that coupling molecules are bound.

After cleaning the surface of the ITO substrate with ethanol, the ITO substrate was immersed in a 10 mmol/L solution of disuccinimidyl suberate (DSS) in DMF at room temperature for eight hours under an Ar atmosphere so that disuccinimidyl suberate was bound as detecting molecules to aminopropyltriethoxysilane.

After the surface of the ITO substrate was washed with DMF and acetone, the ITO substrate was immersed at room temperature for two hours in a 20 mg/mL solution of human serum albumin (HSA: product of Sigma; 97 to 99t (agarose gel electrophoresis lyophilized powder)) in a phosphate buffer so that human serum albumin was bound to a portion of residual groups of disuccinimidyl suberate, the residual groups being bound as modifying molecules to the aminopropyltriethoxysilane, to prepare an electrode for molecular sensing. Because the molecular size of human serum albumin is extremely large, the human serum albumin did not react to all the residual groups of disuccinimidyl suberate in the above-described treatment, and therefore, the portion of the residual groups of disuccinimidyl suberate were modified by the human serum albumin. A schematic of a state that a portion of DSS is modified by HSA is shown in FIG. 1.

<Molecular Sensing>

Immersed in a phosphate buffer (PBS) of pH 7.4 were the above-obtained electrode for molecular sensing as a working electrode (WE), an Ag/AgCl electrode as a reference electrode (RE), and a Pt wire as a counter electrode (CE). The potential ($E_0$) before addition of target molecules was then measured at room temperature in an Ar atmosphere.

D-tryptophan was then added as target molecules such that its concentration in the phosphate buffer became 0.001 mol/L, and the potential (E) was measured at time intervals. Potential shifts ($\Delta E = E - E_0$) are shown in FIG. 4.

Example 10

In a similar manner as in Example 9 except that the target molecules were changed to L-tryptophan, the potential ($E_0$) and potential (E) were measured. Potential shifts ($\Delta E$) are shown in FIG. 4.

Figure 4:
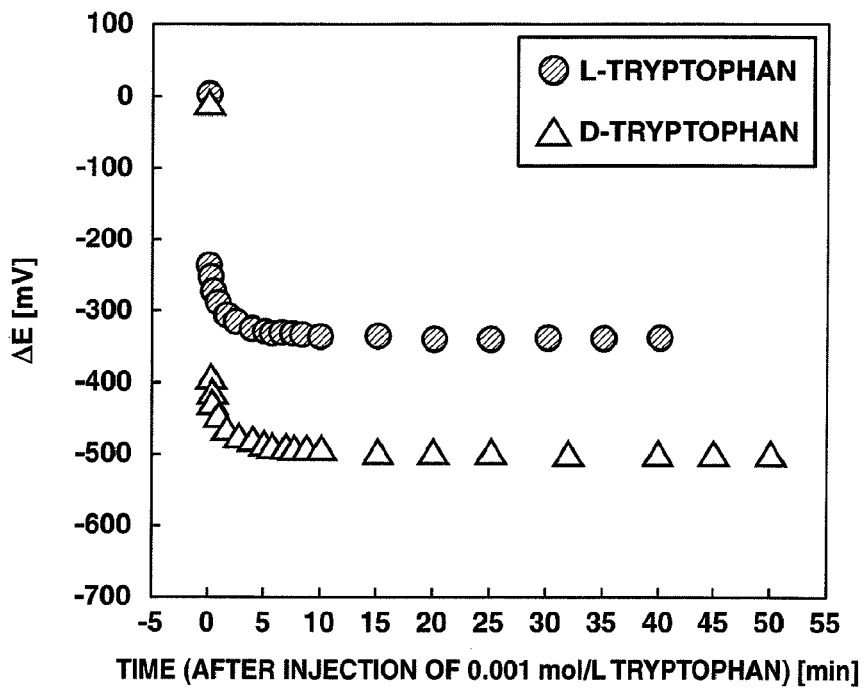
FIG. 4 is a graph showing changes with time in potential shift in Examples 9 and 10.

As shown in FIG. 4, the potential shift is different between D-tryptophan and L-tryptophan, and therefore, it is appreciated that the electrode for molecular sensing according to the present invention is effective for the selective detection of D-tryptophan or L-tryptophan. Further, compared with L-tryptophan, D-tryptophan resulted in greater potential shift. As a reason for this, it may be presumed that, because L-tryptophan has high affinity to HSA, L-tryptophan is more attracted to HSA and the reaction of L-tryptophan to the detecting molecules is interfered by HSA, and as a result, the potential shift becomes small, and that, because D-tryptophan, on the other hand, has low affinity to HSA, D-tryptophan is less attracted to HSA, the reaction of D-tryptophan to the detecting molecules is hardly interfered by HSA, and as a result, the potential shift becomes large.

Examples 11 and 12

In a similar manner as in Example 9 except that the concentration of D-tryptophan in the phosphate buffer was changed to 0.0001 mol/L (Example 11) and 0.01 mol/L (Example 12), respectively, the potential ($E_0$) and potential (E) were measured. The potential shifts ($\Delta E$) at the time points that the potentials no longer changed by ±0.5 mV or more for 5 minutes subsequent to the addition of the D-tryptophan are shown in FIG. 5 together with the results of Example 9.

Examples 13 and 14

In a similar manner as in Example 10 except that the concentration of L-tryptophan in the phosphate buffer was changed to 0.0001 mol/L (Example 13) and 0.01 mol/L (Example 14), respectively, the potential ($E_0$) and potential (E) were measured. The potential shifts ($\Delta E$) at the time points that the potentials no longer changed by ±0.5 mV or more for 5 minutes subsequent to the addition of the L-tryptophan are shown in FIG. 5 together with the results of Example 10.

Figure 5:
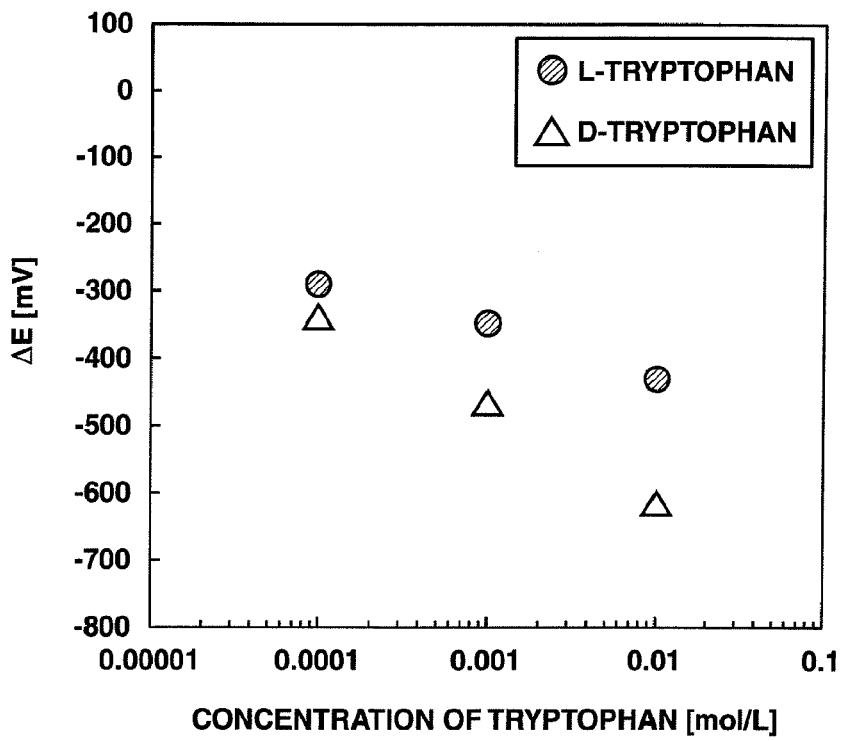
FIG. 5 is a graph illustrating potential shifts in Examples 9 to 14 and showing the concentration dependency of the potential shift on the target molecules.

As the potential shift changes depending upon the concentration of each of D-tryptophan and L-tryptophan as shown in FIG. 5, it is appreciated that the concentration of target molecules can be measured by the molecular sensing of the present invention. It is also appreciated that the difference in potential shift between D-tryptophan and L-tryptophan increases with their concentrations.

Example 15

Figure 6:
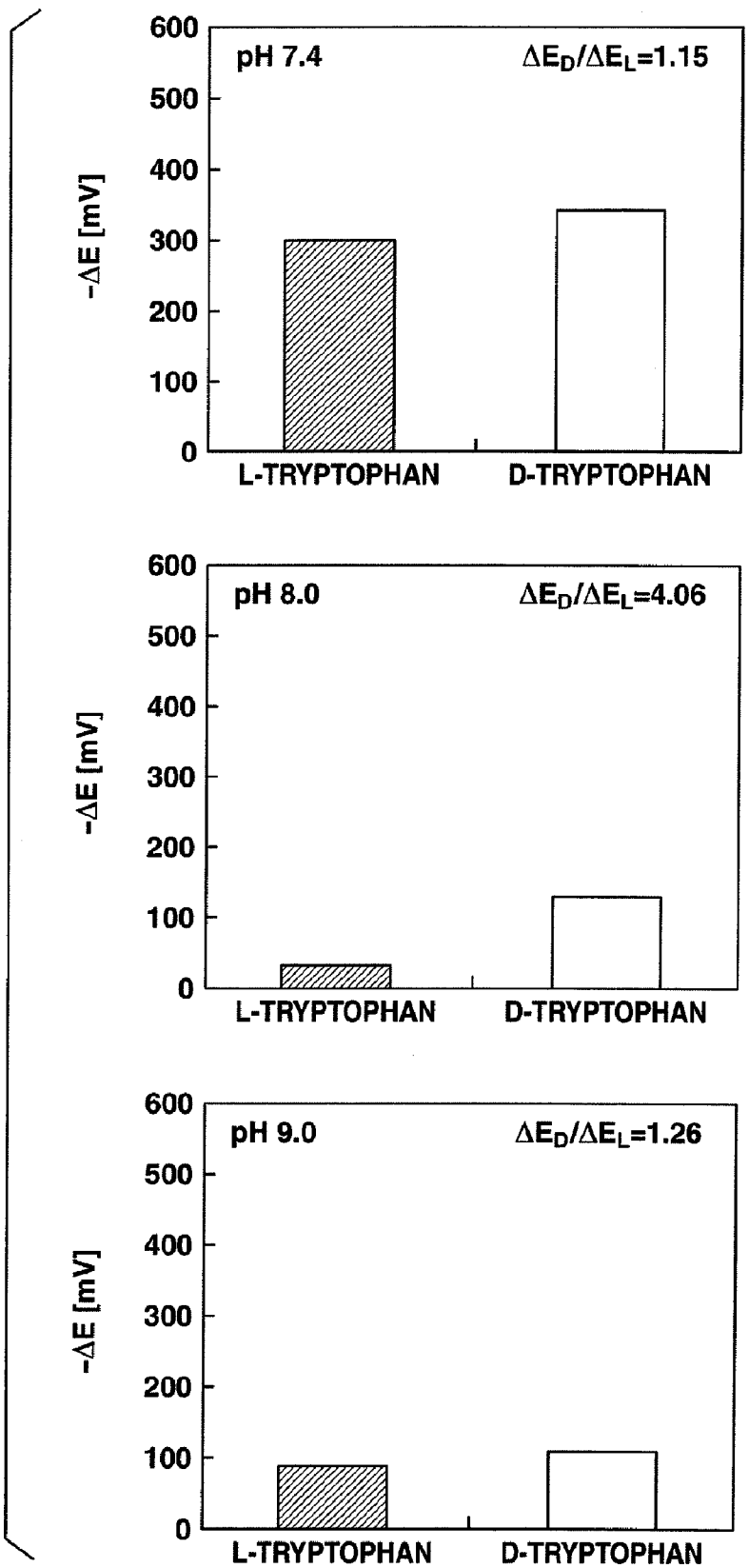
FIG. 6 is a graph illustrating potential shifts in Examples 1, 2 and 15 to 18.

In a similar manner as in Example 11 except for the use of a phosphate buffer (PBS) of pH 8, the potential ($E_0$) and potential (E) were measured. The potential shift ($\Delta E$) at the time point that the potential no longer changed by ±0.5 mV or more for 5 minutes subsequent to the addition of the D-tryptophan is shown in FIG. 6 together with the results of Example 11.

Example 16

In a similar manner as in Example 13 except for the use of a phosphate buffer (PBS) of pH 8, the potential ($E_0$) and potential (E) were measured. The potential shift ($\Delta E$) at the time point that the potential no longer changed by ±0.5 mV or more for 5 minutes subsequent to the addition of the L-tryptophan is shown in FIG. 6 together with the results of Example 13.

Example 17

In a similar manner as in Example 11 except for the use of a borate buffer of pH 9, the potential ($E_0$) and potential (E) were measured. The potential shift ($\Delta E$) at the time point that the potential no longer changed by ±0.5 mV or more for 5 minutes subsequent to the addition of the D-tryptophan is shown in FIG. 6 together with the results of Example 11.

Example 18

In a similar manner as in Example 13 except for the use of a borate buffer of pH 9, the potential ($E_0$) and potential (E) were measured. The potential shift ($\Delta E$) at the time point that the potential no longer changed by ±0.5 mV or more for 5 minutes subsequent to the addition of the L-tryptophan is shown in FIG. 6 together with the results of Example 13.

As shown in FIG. 6, it is appreciated that compared with pH 7.4 or pH 9, pH 8 gives a remarkable difference in potential shift difference ($\Delta E$) between a D-enantiomer and an L-enantiomer, thereby permitting more selective sensing of the enantiomers with higher sensitivity.

The invention claimed is:

1. A method for molecular sensing, which comprises using an electrode for molecular sensing comprising,
   a conductive metal oxide having surface hydroxyl groups, and
   a detecting molecule capable of shifting a surface potential of said electrode when it interacts with at least one indole-ring-containing compound, wherein the detecting molecule is a disuccinimidyl alkylenedicarboxylate having a linear alkylene group of from four to ten carbon atoms that is modified with human serum albumin,
   the indole-ring-containing compound shifts said surface potential by interacting with said disuccinimidyl alkylenedicarboxylate having a linear alkylene group of from four to ten carbon atoms that is modified with human serum albumin and said detecting molecule is bound to the surface hydroxyl groups on the conductive metal oxide via an aminoalkylalkoxysilane, and based on a shift in the surface potential of said electrode, detecting an indole ring-containing compound.

2. The method according to claim 1, wherein said indole-ring-containing compound is tryptophan, tryptamine or indolepropionic acid.

3. The method according to claim 2, wherein said tryptophan, tryptamine or indolepropionic acid is detected in an aqueous solution of pH 7 to 10.

4. A method for molecular sensing, which comprises using an electrode for molecular sensing as defined in claim 1, and based on a shift in the surface potential of said electrode, selectively detecting a D-enantiomer or L-enantiomer of said indole ring-containing compound.

5. The method according to claim 4, wherein said indole-ring-containing compound comprising an enantiomer is tryptophan.

6. A method for molecular sensing comprising, using an electrode for molecular sensing and based on a shift in a surface potential of said electrode, selectively detecting D-tryptophan or L-tryptophan, wherein said shift in said surface potential is different depending upon whether D-tryptophan or L-tryptophan interacts with said electrode and said electrode comprises:
   a conductive metal oxide having surface hydroxyl groups, and
   a detecting molecule capable of shifting said surface potential of said electrode when it interacts with D-tryptophan or L-tryptophan, wherein the detecting molecule is a disuccinimidyl alkylenedicarboxylate having a linear alkylene group of from four to ten carbon atoms that is modified with human serum albumin and said detecting molecule is bound to said surface hydroxyl groups on said conductive metal oxide via an aminoalkylalkoxysilane,
   wherein the D-tryptophan or L-tryptophan shifts said surface potential by interacting with said disuccinimidyl alkylenedicarboxylate having a linear alkylene group of from four to ten carbon atoms that is modified with human serum albumin.

7. The method according to claim 6, wherein said D-tryptophan or L-tryptophan is detected in an aqueous solution of pH 7 to 10.

8. The method according to claim 1, wherein said conductive metal oxide is indium tin oxide, tin oxide, indium oxide or zinc oxide.

9. The method according to claim 4, wherein said conductive metal oxide is indium tin oxide, tin oxide, indium oxide or zinc oxide.

10. The method according to claim 6, wherein said conductive metal oxide is indium tin oxide, tin oxide, indium oxide or zinc oxide.

* * * * *